United States Patent [19]

Mutterle et al.

[11] Patent Number: 5,388,690
[45] Date of Patent: Feb. 14, 1995

[54] PROPORTIONING DEVICE FOR EXTEMPORANEOUS MULTIDOSE SYRUPS

[75] Inventors: Antonio Mutterle, Breganzona, Switzerland; Elisabetta Donati-Pedemonti, Breccia, Italy

[73] Assignee: IBSA Institut Biochimique S.A., Lugano, Switzerland

[21] Appl. No.: 152,727

[22] Filed: Nov. 15, 1993

[30] Foreign Application Priority Data

Nov. 27, 1992 [IT] Italy .................. MI92 U 001016

[51] Int. Cl.⁶ .................. B65D 25/08; B67D 5/00
[52] U.S. Cl. .................. 206/222; 215/DIG. 8; 222/83
[58] Field of Search .................. 206/219, 221, 222; 215/DIG. 8; 222/80, 81, 83

[56] References Cited

U.S. PATENT DOCUMENTS

| | | | |
|---|---|---|---|
| 3,603,469 | 9/1971 | Magni | 215/DIG. 8 |
| 3,768,697 | 10/1973 | Lemer | 222/80 |
| 3,802,604 | 4/1974 | Morane et al. | 222/83 |
| 4,067,440 | 1/1978 | Lataix | 206/222 |
| 4,465,183 | 8/1984 | Saito et al. | 206/222 |
| 4,682,689 | 7/1987 | Pereira et al. | 206/222 |
| 4,757,916 | 7/1988 | Goncalves | 222/83 |
| 4,884,705 | 12/1989 | Debetencourt | 222/83 X |

FOREIGN PATENT DOCUMENTS

| | | |
|---|---|---|
| 0069892 | 1/1983 | European Pat. Off. . |
| 0217425 | 4/1987 | European Pat. Off. . |
| 0251193 | 1/1988 | European Pat. Off. . |
| 0344849 | 12/1989 | European Pat. Off. . |
| 2289407 | 9/1975 | France . |
| 505736 | 5/1971 | Switzerland . |

Primary Examiner—Bryon P. Gehman
Attorney, Agent, or Firm—Hedman, Gibson & Costigan

[57] ABSTRACT

Proportioning device for extemporaneous multidose syrups, comprising a fluid container and a closing plug containing the active principle in subdivided solid form and made up by a tray, a hood and a perforator coaxial and internal with respect to the hood, the closing plug being separated from the container by means of diaphragm which is perforated the moment when the active principle falls into the fluid and the hood being removable and utilizable as a measure.

6 Claims, 2 Drawing Sheets

PROPORTIONING DEVICE FOR EXTEMPORANEOUS MULTIDOSE SYRUPS

PRIOR ART

In the pharmaceutical field there are numerous active principles whose stability has a short life span once they have been introduced in an aqueous environment. When however said active principles have to be administered in form of syrup, for instance to permit the adjustment of the dosage to patient's needs, the pharmaceutical technician formulates the preparation in form of dry syrup.

This pharmaceutical form is made up by a bottle containing a granular or powdery product to which the patient or the chemist adds drinking water up to a preset level, marked on either the bottle or the label. The addition of water can be made in a preset quantity by means of a special calibrated proportioning beaker. While the anhydrous form has a stability which generally lasts for several months, the reconstituted form remains stable fop no more than a few days and often requires to be preserved in a refrigerator.

Water addition to dry syrups is a critical point of this pharmaceutical form, and in particular:

the water utilized may not be drinkable, especially in third world countries; besides, the water utilized, even though it may be bacteriologically pure, may contain mineral salts that can alterate the drug;

the total volume may oscillate greatly, as water addition is made difficult by the label which covers the bottle almost completely. Besides, in adding water, alp bubbles may form within the granular product, which distort the volume of the fluid and which when the latter is shaken cause the formation of foam layers which hinder a correct assessment of the level. In this case, the patient stops adding water too soon, which involves that the drug administered has a concentration higher than the prescribed posology;

the same problem occurs with presentations having a separate water proportioner. Introducing water with the proportioner is no easy operation, and fluid losses often take place duping the pouring, with the already described consequences of an increased drug concentration or an empirical reintegration of water by the patient, alternating in this way the final volume.

These drawbacks, which produce incorrect syrup dosages, may turn out to be particularly harmful and dangerous in case of antibiotics administration.

The pharmaceutical market offsets several preparations which are presented in monodose bottles.

The hydrosensitive active principle in form of powder is contained in the proportioning plug which is perforated just before the administration, allowing the powder to solubilize or disperse in the syrup below. The bottle has a drawback in that it can contain, because of its size, only the volume of one single dose.

SUMMARY

We have now found a proportioning device for extemporaneous syrups which permits to overcome the drawbacks of the prior art advantageously, and which also permits an easy reconstitution of the syrup. With reference to FIG. 1, said proportioning device comprises a container D for the fluid, and a closing plug containing the active principle in subdivided solid form constituted by a tray C, a hood A and a perforator B coaxial and internal with respect to said hood A, said tray C being divided in two sectors, a lower sector tightly fixed on the mouth of said container D and an upper sector in which said hood A and said perforator B engage telescopically, said closing plug being separated from said container by means of a diaphragm 10 which is perforated the moment one wishes the active principle to fall into the fluid, and said hood being removable and utilizable as a measure.

Said device permits the administration in subsequent times of several doses, which are measured utilizing the hood A as a measure, with a great advantage in use, and, besides, it offers the advantage of an easy fabrication and assembly of the components.

DETAILED DESCRIPTION OF THE INVENTION

The characteristics and advantages of the proportioning device for extemporaneous multidose syrups for pharmaceutical use according to this invention will be illustrated with more details in the following description.

BRIEF DESCRIPTION OF THE DRAWINGS

The device object of this invention is shown in FIGS. 1 and 2, of which.

DESCRIPTION OF THE PREFERRED EMBODIMENT

Figure 1:
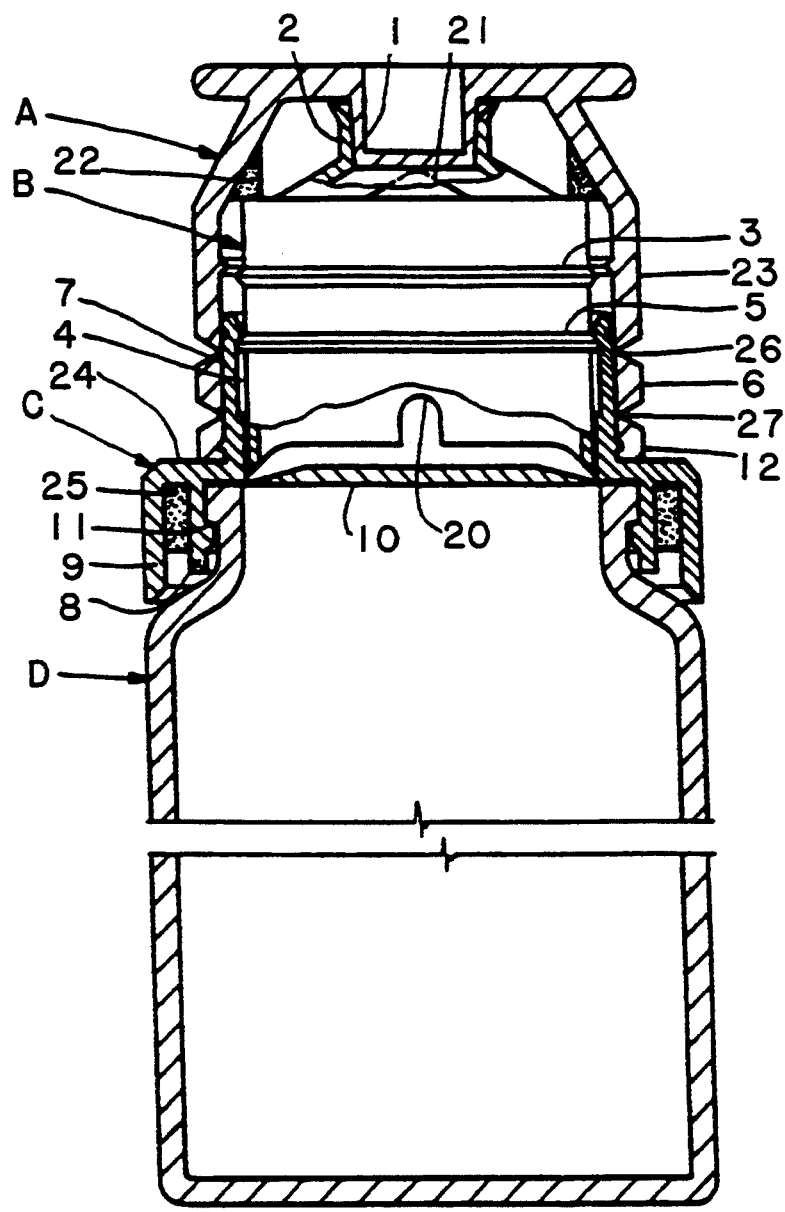
FIG. 1 is a longitudinal section of the device before the use, but ready for use.
Figure 2:
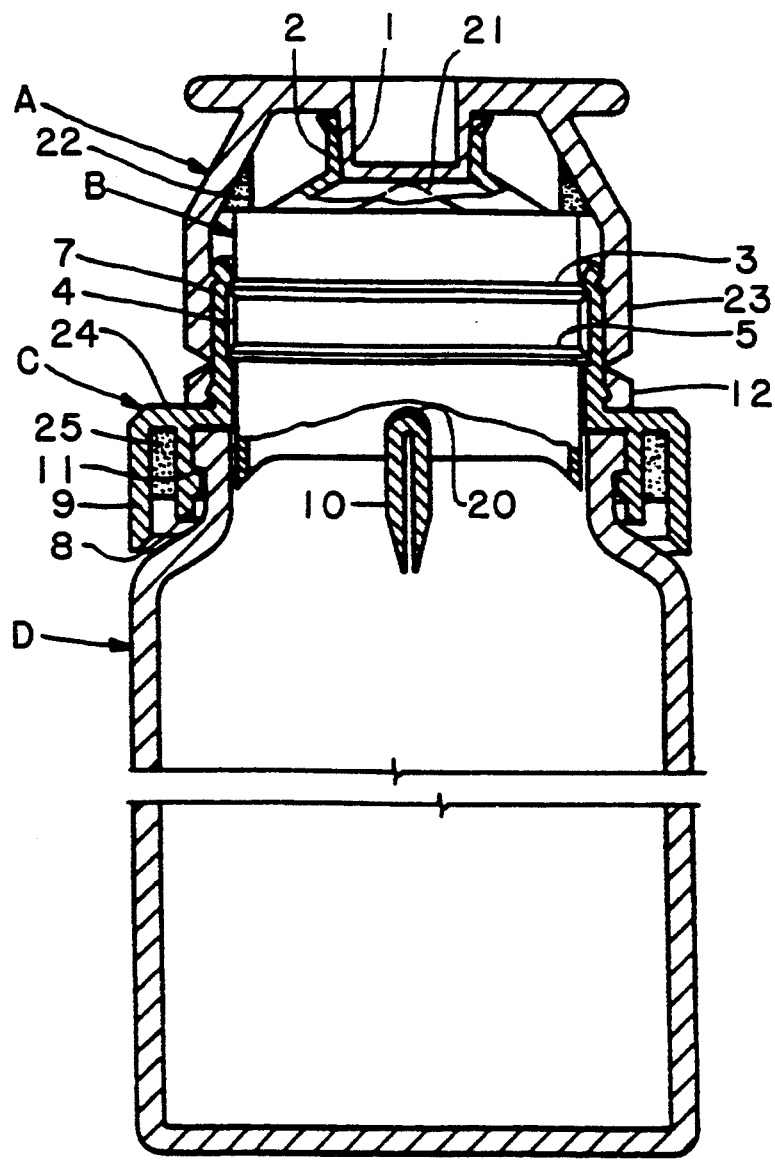
FIG. 2 is the same device once the perforator has been pushed down, perforating the diaphragm 10 and causing the fall of the active principle into the fluid below.

The device comprises two elements, namely a container D and a closing plug constituted by a tray C, a perforator B and a hood A. Tray C, which has a bigger diameter lower sector and a smaller diameter upper sector, united through the horizontal base 24, is applied at the mouth of said container. The lower sector is fixed to the wall of the mouth of container D by means of a ring-step 11, and ensures the tightness against the base of the mouth thanks to the interposition of the marginal sector of diaphragm 10. Diaphragm 10 is constituted by a polythene membrane coupled to an aluminium/polythene film; the latter permit to ensure the tightness between the fluid contained in the container D and the (hydrosensitive) subdivided solid contained in the closing plug. Diaphragm 10 closes at the bottom perforator B in which the active principle is loaded in form of powder or granules, and separates it tightly from container D where the fluid for the solution or the dispersion of the active principle is contained.

The lower sector of said tray is made up by two cylinder-shaped coaxial elements 8 and 9, stiflened by internal baffles 25 and connected to one another through the horizontal base 24. A structure forms, suitable for withstanding the pressure exerted on said base during the assembly, and which has a good aesthetical appearance.

The upper sector is made up by a cylinder-shaped element 7 equipped, in correspondence with the upper edge, with a ring-indentation 4, and fit for engaging with perforator B on the inside, and hood A on the outside.

Perforator B is made up by a cylinder-shaped structure having in the lower part a dove-tailed cutting edge, interrupted by two windows 20 diametrally opposite to one another, in correspondence of which the diaphragm is not cut during the reconstitution. This permits to fold the diaphragm on itself and to keep it blocked in correspondence of its diameter. In this way the diaphragm cannot fall into the fluid below, nor can it obstruct the mouth of the bottle during the pouring. In correspondence of said cutting edge, diaphragm 10 has a weakening ring to make perforation easier. On the external surface, the perforator has two ring-steps 3 and 5, which limit the travel within the upper sector of the tray.

At the upper end, it has a cylinder-shaped mouth 2 for clutching in indentation 1 of hood A, characterized by a drip-catching flared rim, suitable for pouring the fluid.

Hood A comprises three sectors: an upper truncated conic cylindrical sector 23 whose base projects with respect to the truncated conic base; an intermediate sector made up by a ring-band 6 easily removable in that it adheres to the upper sector and to the lower sector by means of circumference weakened lines 26 and 27, and equipped also with a tongue, to make hold and traction easier; a lower ring-sector 12 resting on the base of the tray.

The device object of this invention has, among others, the advantage of being assemblable by means of high-speed automatic machines which provide to dosing and loading the active principle and the fluid, as well as to the assembly of the various parts.

In detail, hood A, already assembled with perforator B, is turned upside down, to contain the necessary quantity of active principle. Tray C is assembled on to the A/B complex, forming the "container-plug" device which shall be assembled, in its turn, to container D, previously filled with the constitution fluid.

To utilize the syrup, ring-band 6 is taken off, causing in this way the overlying part 23 of hood A to slide downwards. By exerting a pressure on the base of A, the whole A and B goes down and perforates diaphragm 10 which is taken up in windows 20 and the active principle falls down and solves or disperses in the fluid below. After the reconstitution phase of the syrup, the perforator, which up to this point had been an integral part of hood A, becomes integral with tray C and permits to pour the syrup through its flared cylindrical drip-catching mouth.

Now, part 23 of hood A is removed which constitutes a proportioning small beaker or measure, and the first dose of the syrup to be administered is poured in it. Afterwards, the proportioning beaker is reintroduced as a cover of the device until the second dose is taken, and so on.

The removal of element 23 of the hood from mouth 2 of the perforator is made easier by the presence of pairs of elements 21 and 22, on the external surface of the perforator and the internal surface of the hood, respectively. Element 21 is tilt-bed shaped and element 22 is tongue-shaped. The rotation of element 23 causes tongue 22 to slide along tilt-bed 21 and at the same time said element 23 goes up again. The pairs of elements 21 and 22 are in number of two or three, arranged along the circumference at 180° or 120° respectively.

Container D has a volume that permits to load in it the quantity of fluid necessary to the reconstitution of the syrup.

Measure 23 has a volume that permits to load in it the unity dose of syrup, for instance from 2 ml to 15 ml.

Hence, the device object of this invention allows the administration of the number of doses required according to order, during the period of validity of the reconstituted syrup.

The following are the construction materials of the various components of the device object of this invention:

glass or plastic material for container D;
polyethylene or other plastic material for tray C;
polypropylene or other plastic material for perforator B;
polyethylene or other plastic material for hood A;
polyethylene-aluminium coupling for diaphragm 10;

All of the materials that constitute the invention can be sterilized by irradiation or exposure to ethylene oxide, which permits to confect the preparation in sterile conditions.

Many variants may be introduced in the device object of this invention, without overstepping its claim field. In particular, an embodiment may be considered in which the plug is screw-coupled to the container, always in keeping with the spirit of the invention. The fluid loaded in the container D may be constituted by simple purified water or a simple placebo sucrose-syrup or other acariogenic sugars or a medicated syrup containing a non-hydrosentitive active principle.

Preferred placebo syrups have For instance the following composition:
PLACEBO SYRUP 1: maltitol solution, aromatizers, sweeteners, and/or pH correctors, purified water;
PLACEBO SYRUP 2: sucrose, aromatizers, sweeteners, and/or pH correctors, purified water.

Numerous active principles may be advantageously used for extemporaneous syrups utilizing the device object of this invention, and in particular, for instance, the following:
Amoxicillin compact;
Amoxicillin powder, disgregants, fluidizers and wetteners; constituents are dry-mixed;
Amoxicillin powder, disgregants, wetteners and diffusers; constituents are wet-granulated;
Amoxicillin powder, disgregants, wettenets and diffusers; constituents are dry-granulated;
Cephalexin compact;
Cephalexin powder mixed with suitable excipients: disgregants, wetteners, diffusers and fluidizers;
Doxycycline compact;
Doxycycline powder mixed with suitable excipients;
Ampicillin compact;
Ampicillin powder mixed with suitable excipients;
Vitamin complexes;
Naproxen powder;
Naproxen mixed or granulate with suitable excipients;
Mefenamic Acid powder;
Mefenamic Acid mixed or granulate with suitable excipients;
Doxylamine succinate powder or mixture with suitable excipients;
N-acetylcysteine powder.

The examples hereabove are not to be construed as a limitation and only refer to some therapeutical classes. The proportioning device, object of this invention, may actually be used For any active principle which can be administered in form of syrup.

It ensues from the above description that the use of the device object of this invention is extremely advantageous. In fact, the mixing of the active principle with the fluid is carried out in a practical and safe way, without interventions by the chemist or the patient, and the latter benefits from at least four advantages:

he performs an objectively easy and safe operation, which is important in particular with old people;

he does not run the risk of mistaking the dosage, causing the product to be dangerous;

he does not risk to pollute the product with unsuitable water;

he does not expose the product to microbiologic pollution risks.

We claim:

1. Proportioning device for extemporaneous multidose syrups for pharmaceutical use, which allows the assembly in one single structure of all of the constituents of a syrup, comprising a container (D) for a fluid, said container having a mouth, and a closing plug containing an active principle in subdivided solid form, characterized in that said closing plug is constituted by a tray (C), a hood (A) and a perforator (B) coaxial and internal to said hood said tray being distinct in two sectors, a lower sector tightly fixed on said mouth of said container and an upper sector in which said hood and said perforator engage telescopically, said closing plug being separated from said container by means of a diaphragm (10) which is perforated at the moment the active principle is to be added to said fluid said perforator having a dove-tailed cutting edge interrupted by two windows (20) which are diametrically opposite to one another and interrupt said dove-tailed cutting edge and said windows being adapted to engage said diaphragm in a folded condition after said diaphragm is cut and folded by said perforator.

2. Device according to claim 1, wherein the edges of said diaphragm provide a tight seal between said container and said closing plug.

3. Device according to claim 1, wherein said lower sector of said tray is constituted by two coaxial cylindric elements stiffened by internal sections and connected to one another by means of a horizontal tray base.

4. Device according to claim 3, wherein said hood is constituted by a truncated conic cylindric upper sector having a base which projects with respect to said truncated conic cylindric upper sector, and an intermediate sector constituted by an easily removable band, and a lower sector which rests on said horizontal tray base.

5. Device according to claim 1 wherein said hood is removable and utilizable as a measure.

6. Device according to claim 1 wherein said diaphragm has a weakening ring to make perforation easier.

* * * * *